United States Patent [19]

Takamura et al.

[11] Patent Number: 4,677,471
[45] Date of Patent: Jun. 30, 1987

[54] ENDOSCOPE

[75] Inventors: Koji Takamura; Haruhiko Kaiya, both of Tokyo, Japan

[73] Assignee: Olympus Optical Co., Ltd., Tokyo, Japan

[21] Appl. No.: 893,270

[22] Filed: Aug. 5, 1986

[30] Foreign Application Priority Data

Aug. 16, 1985 [JP] Japan .................... 60-180219
Oct. 3, 1985 [JP] Japan .................... 60-151642

[51] Int. Cl.⁴ .................... H04N 7/18; A61B 1/04; A61B 1/06
[52] U.S. Cl. .................... 358/98; 128/6; 358/229; 358/167
[58] Field of Search .................... 358/98, 229, 245, 93, 358/100, 167; 128/4, 6

[56] References Cited

U.S. PATENT DOCUMENTS

| | | | |
|---|---|---|---|
| 4,218,712 | 8/1980 | Clymer | 358/229 |
| 4,223,355 | 9/1980 | Lerch | 358/229 |
| 4,301,790 | 11/1981 | Bol | 358/98 |
| 4,344,092 | 8/1982 | Miller | 358/98 |
| 4,491,865 | 1/1985 | Danna | 358/98 |
| 4,517,494 | 5/1985 | Yasui | 358/245 |
| 4,600,940 | 7/1986 | Sluyter | 358/98 |
| 4,618,885 | 10/1986 | Nagasaki | 358/98 |

Primary Examiner—Howard W. Britton

[57] ABSTRACT

An endoscope is disclosed which includes a lens unit having a lens frame and lens frame cover and plurality of lenses attached to the lens frame, and image sensor unit located behind the lens frame. The image sensor unit comprises an electroconductive image sensor housing whose forward end portion is attached to the outer periphery of a rear end portion of the lens frame and which has a recess at the rear end portion, electric circuit section comprised of a solid-state image sensor fitted into the recess of the image sensor housing and having a plurality of lead-in pins and electric circuit components electrically connected to the lead-in pins, electroconductive shield pipe attached at a forward end portion to the outer periphery of the rear end portion of the image sensor housing, having a rearwardly extending rear end and including the whole electric circuit section therein, a cable fixing frame located behind an electric circuit section, fixed to the rear end portion of the shield pipe with an electroconductive pipe holder and having a through recess or recesses, and shielding wires inserted into the shield pipe and each having an outer cover, external conductors, and internal conductors electrically connected to associated electric components or lead-in pins.

14 Claims, 14 Drawing Figures

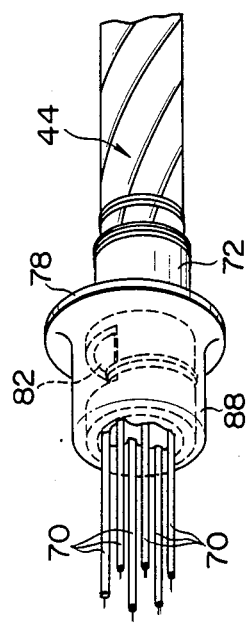
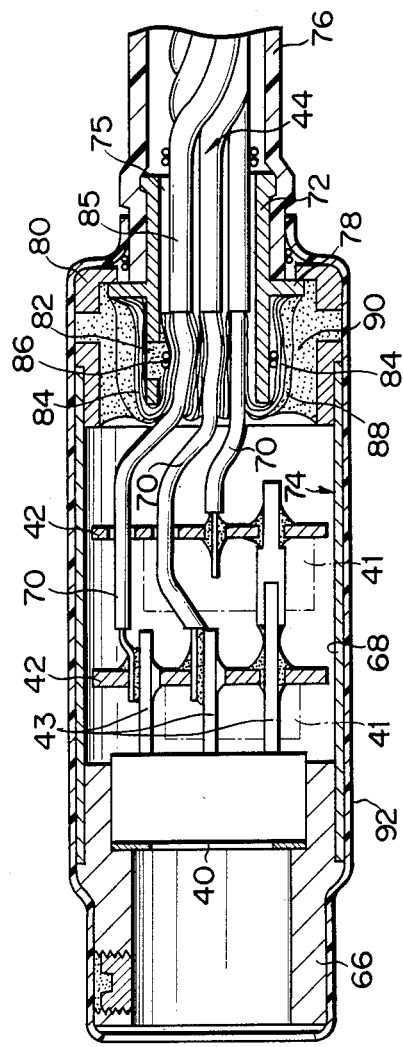
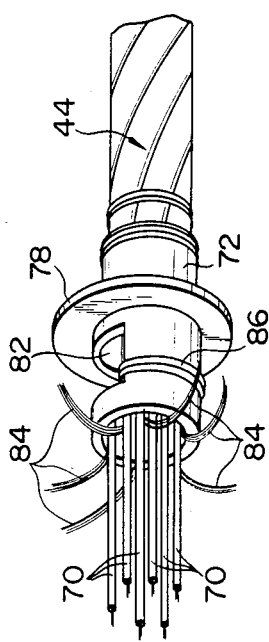

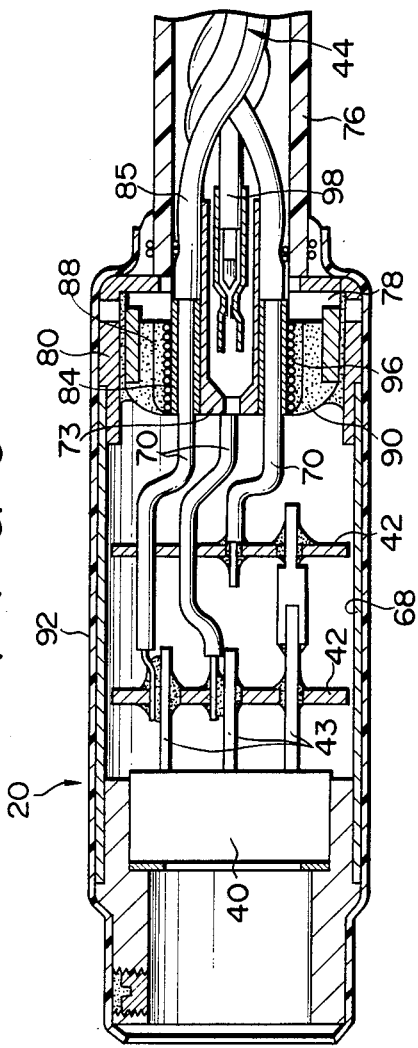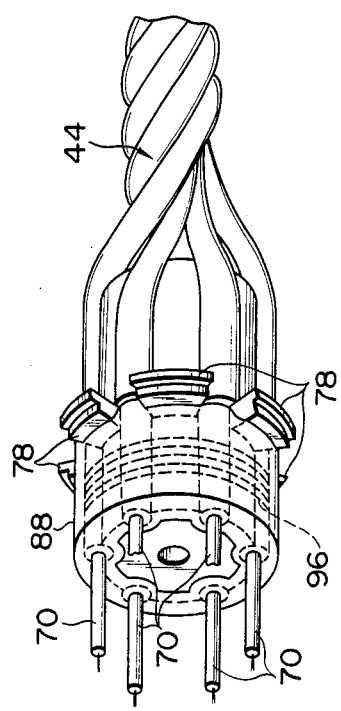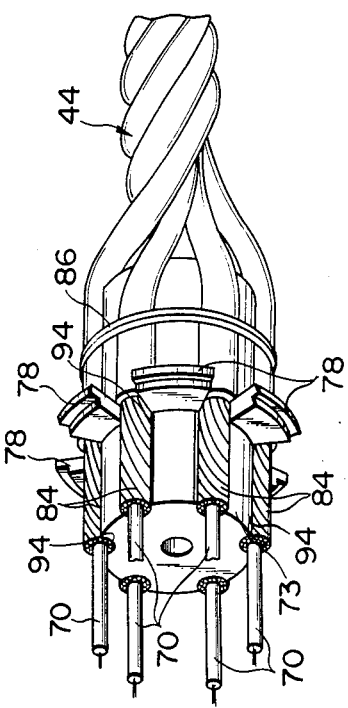

F I G. 11
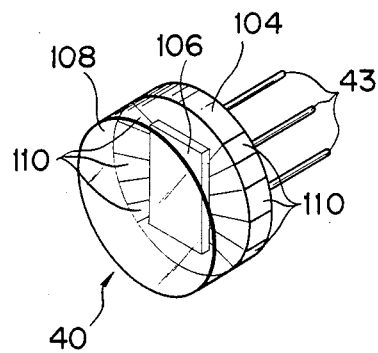
F I G. 12
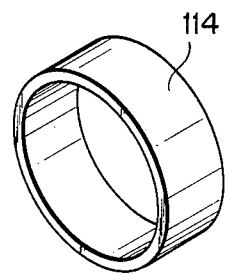
F I G. 13
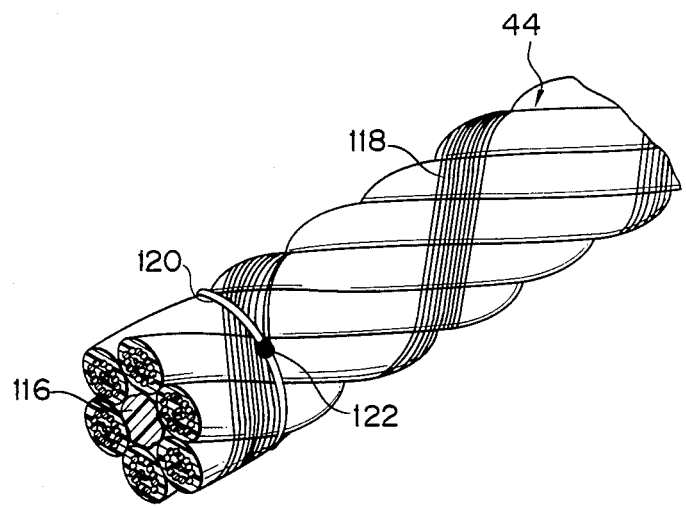

ENDOSCOPE

BACKGROUND OF THE INVENTION

1. Field of the Invention

This invention relates to an endoscope to be inserted into a region of interest of a human subject and, in particular, to an endoscope having at a distal end portion a solid-state image sensor to which shielding wires are connected as a signal cable.

2. Description of the Prior Art

A conventional endoscope is disclosed, for example, in Japanese Patent Disclosure (KOKAI) Nos. 55-54933 and 58-69528. This endoscope includes an image sensor unit equipped with a solid-state image sensor as an observation means to which shielding wires are connected in the form of a signal cable. In this case, the forward ends of the shielding wires are electrically connected to the lead-in terminals or a substrate of the solid-state image sensor.

When the endoscope is inserted into a region of interest of a human subject, the insertion section of the endoscope is bent and thus a protective tube containing a cable is also curved, with the result that the cable, interconnection between the cable and the substrate, and/or interconnection between the cable and the lead-in terminals of the solid-state image sensor undergo an external force. This may involve a risk of the associated components being separated from the corresponding interconnection areas.

In the neighborhood of the solid-state image sensor of the conventional endoscope, an amplifier is usually provided to amplify a signal from the solid-state image sensor. Where, however, the solid-state image sensor and associated amplifier are not adequately shielded, they are liable to suffer an external noise. Particularly where an electrical device, such as a high-frequency treatment device, is employed together with this endoscope, a noise emerges on the screen of a monitor, failing to adequately observe the region of interest of a human subject.

SUMMARY OF THE INVENTION

An object of this invention is to provide an endoscope which can protect an electric circuit section, including a solid-state image sensor in an image sensor unit, against an external noise, whereby even when a high-frequency treatment device is used within a channel of the endoscope, a monitor screen is not disturbed due to a noise from current of a high frequency.

Another object of this invention is to provide an endoscope which, even when shielding wires of a cable for an electric signal transmission system undergo an external force, transmits no external force to an interconnection area of internal conductors of the shielding wires so that an adequate structural strength is assured.

Another object of this invention is to provide an endoscope of adequate safety which electrically insulates the outer periphery of a solid-state image sensor body and prevents a short-circuiting from occurring between the solid-state image sensor and an associated member and thus prevents a breakage of the solid-state image sensor.

These objects of this invention are achieved by an endoscope as set forth below.

According to this invention an endoscope is provided which comprises:

(1) an optical lens unit including a lens frame having a rear end portion, and lens frame cover and a plurality of lenses attached to the lens frame; and (2) an image sensor unit attached to an outer periphery of the rear end portion of the lens frame and comprising, (a) an electroconductive image sensor housing, one forward end portion of which is attached to the outer periphery of the rear end portion of the lens frame, the image sensor housing having a rear end portion and a recess formed there;

(b) an electric circuit section comprised of a solid-state image sensor located within the recess and having a plurality of lead-in pins, and electric component parts electrically connected to the lead-in pins;

(c) an electroconductive shield pipe attached at a forward end portion to the outer periphery of the rear end portion of the image sensor housing and having a rearwardly extending rear end portion, the shield pipe containing the whole electric circuit section therein;

(d) electroconductive cable fixing member located behind the electric circuit section and having through recess means, the cable fixing member being fixed to the rear end portion of the shield pipe with a pipe holder therebetween; and (e) shielding wires inserted into the shield pipe through the recess and each having an outer cover, external conductors and internal conductors electrically connected to the electric component parts or the lead-in pins.

Furthermore, the outer covers of the shielding wires are stripped in the neighborhood of the cable fixing member to provide exposed external conductors so that the exposed external conductors are electrically connected, and firmly bonded, to the cable fixing member.

Furthermore, an electrically insulating member is attached to the outer periphery of the solid-state image sensor to provide an integral unit which is fitted in the recess of the image sensor housing.

BRIEF DESCRIPTION OF THE DRAWINGS

FIG. 2 is a cross-sectional view in side elevation showing an image sensor unit of the endoscope of FIG. 1;

FIGS. 3 and 4 each are a perspective view showing the neighborhood of a cable fixing means of the image sensor unit;

FIG. 5 is a cross-sectional view in side elevation showing an image sensor unit of an endoscope according to a second embodiment of this invention;

FIGS. 6 and 7 each are a perspective view showing the neighborhood of a cable fixing means of the endoscope of FIG. 5;

FIG. 11 is a perspective view showing the solid-state image sensor of the image sensor unit of FIG. 10;

FIG. 12 is a perspective view showing a ring-like insulation member of the image sensor unit of FIG. 11;

FIG. 13 is a perspective view showing a variant of bundled shielding wires of the image sensor unit, the bundled shielding wires being sectioned at one end portion.

DETAILED DESCRIPTION OF THE PREFERRED EMBODIMENT

The embodiments of this invention will be described below with reference to the accompanying drawings.

Figure 1:
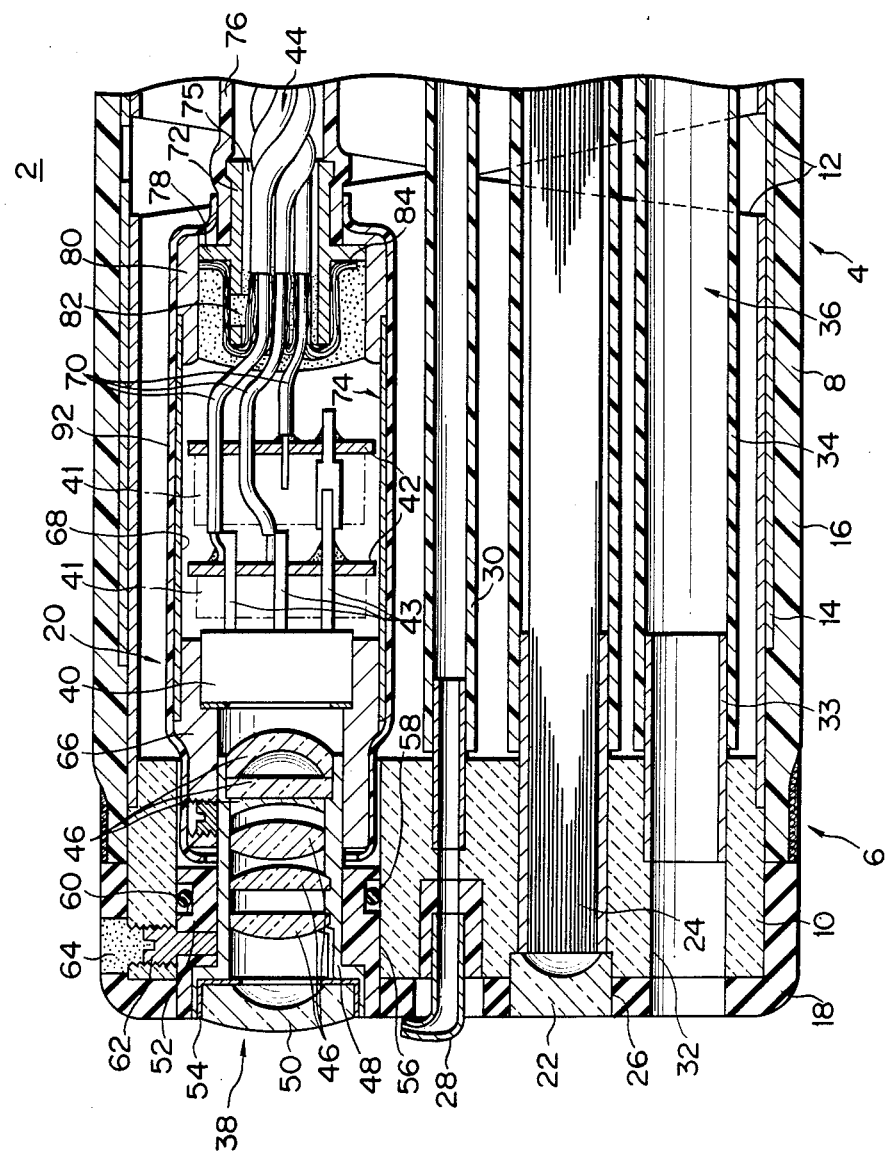
FIG. 1 is a cross-sectional view in side elevation showing an endoscope according to one embodiment of this invention.

FIGS. 1 to 4 show an endoscope according to a first embodiment of this invention. As shown in FIG. 1, distal end portion 6 of insertion section 4 of endoscope 2 has second flexible tube 8 connected to the forward end of a first flexible tube, not shown, and forward end member 10 connected to flexible tube 8. Various kinds of members are incorporated in forward end member 10. Forward end member 10 may be made of a metal, preferably a synthetic resin or ceramics.

Second tube 8 is made of a synthetic resin of an electrical insulating property and contains a plurality of cylindrical members 12 connected to each other as one unit to be bendable. In this case, the unit is inserted into second flexible tube 8 through a blade (14).

Distal end cover 18 is intimately fixed to the front end and outer peripheral surface portion of forward end member 10 and made of an electrically insulating material. Lens unit 38 and image sensor unit 20 are detachably mounted on distal end member 10. Illumination lens 22 is firmly mounted on forward end member 10 in a direction parallel to image sensor unit 20 with the front end of light guide 24 coupled to the inside surface of illumination lens 22, noting that light guide 24 is comprised of an optical fiber bundle. Light guide 24 extends through the forward end member and connected to the forward end member in the neighborhood of the distal end portion of the endoscope. Illumination lens 22 is fitted into hole 26 which extends through the distal end cover.

Air/water supply nozzle 28 is provided at forward end member 10 such that it extends outward through distal end cover 18. Air/water tube 30 is connected to nozzle 28 and nozzle 28 is made of a metal covered by an electrically insulating material, preferably electrically insulating materials.

Channel 32 extends through the forward end member and is connected to channel tube 34 through adapter 33 to provide a continuous channel through which various kinds of treating devices or instruments can be inserted.

Image sensor unit 20 is comprised of solid-state image sensor 40, first and second substrates 42 and 42 on which a plurality of electronic parts or components are mounted as an associated circuit, and a plurality of shielding wires 44 are connected to these substrates. For example, electronic parts or components, such as transistors, capacitors and resistors, are attached to substrate 42. Lens unit 38 has a plurality of optical lenses firmly fixed in place within metal lens frame 48 and cover lens 50 is fixed to the forward end of lens frame 48. Lens frame cover 52 is made of an electrically insulating property and firmly fixed to the outer periphery of lens frame 48. A potting material (54) is fitted at a location between cover lens 50 and lens frame cover 52 such that it also covers the outer periphery of cover lens 50 for sealing.

Solid-state image sensor 40 is fitted in a recess formed at the rear portion of cylindrical image sensor housing 66 made of a metal. The forward end portion of housing 66 is jointed to an outer periphery of the rear end portion of lens frame 48 by means of an electroconductive adhesive. Lens frame cover 52 is mounted on the outer periphery of the forward end portion of lens frame 48.

Substrates 42 and 42 electrically connected to solid-state image sensor 40 are surrounded by shield pipe 68 attached to the outer periphery of the rear end portion of housing 66. Shield pipe 68 is electrically connected to housing 66 and extends rearward such that it covers a connection section of internal conductors 70 of shielding wires 44. Fixing frame 72 made of a metal is fixed relative to the rear end of shield pipe 68 through metal pipe holder 80 with the use of an electroconductive adhesive, so that the fixing frame communicates with shield pipe 68. As a result, lens frame 48, housing 66, shield pipe 68 and fixing frame 72 are electrically connected to each other and constitute cylindrical shield member 74 whereby all the electrical circuit components are electrically shielded. Protective tube 76 for the shielding wire is mounted around the outer periphery of the rear end of fixing frame 72 and sufficiently covers a bending portion of shielding wires 44. Respective shielding wires 44 extend through protective tube 76 into the proximal end of the endoscope and then to a video processing circuit, not shown.

Fixing frame 72 is formed of a cylindrical member and has a flange 78 on the outer periphery of the middle portion, as shown in FIG. 2, such that it is integral with the flange. The flange is attached to shield pipe 68 through pipe holder 80. Fixing frame 72 serves as an electric conductor against shield members 74, such as shield pipe 72. As shown in FIG. 3, cutout 82 is formed on one side portion of cylindrical fixing frame 72, i.e., ahead of the flange 78 of fixing frame 72 to allow shielding wires 44 inserted into bore 75 of the fixing frame to be tied there by yarn. Shielding wires 44 inserted into bore 75 of fixing frame 72 have their outer covers 85 stripped partway of bore 75 to expose external conductors 84. The respective conductors are temporarily tied, by the yarn, around the cutout, i.e., around that portion of fixing frame 72. As shown in FIG. 3, external conductors 84 are outwardly bent, as shown in FIG. 3, along the end of fixing frame 72 with their forward ends reaching the flange (78) as shown in FIG. 2. Then, solder 88 in a molten state is preparatively penetrated through the cutout 82 into the fixing frame 72 to secure the external conductors to the fixing frame. FIG. 4 shows an outer appearance with the set solder (88) covered on the outer surface of the forward end section of fixing frame 72. Furthermore, fixing frame 72 is fixed by another solder 90 to pipe holder 80. Respective internal conductors 70 are connected to substrates 42 or lead-in terminals 43 of the solid-state image sensor 40.

Heat-shrinkable tube 92 made of an electrical insulation is intimately bonded to an outer periphery of housing 66, shield pipe 68 and pipe holder 80. Tube 92 is bonded at its forward end portion to the forward end portion of housing 66 which is attached to the outer periphery of the rear end portion of lens frame 48. Tube 92 is bonded at its rear end portion to the outer periphery of protective tube 76 which is attached to the outer periphery of fixing frame 72.

In the aforementioned arrangement, external conductors of the shielding wires 44 are soldered to fixing frame 72. Thus, an external force which is exerted over shielding wires 44 is borne by fixing frame 72 through external conductors 84. Those stripped portions of external conductors 84 are mostly soldered to have a much higher strength than that of internal conductors 70. As a result, the bonded portion of the shield wires can adequately bear the external force when insertion section 4 of the endoscope is bent or when tube 8 is curved.

FIGS. 5 to 7 show an endoscope according to a second embodiment of this invention. As shown in FIG. 6, cable fixing member 73 has a plurality of grooves, semi-circular in cross section, extending in the axial direction along the outer periphery thereof and respective wires 44 are each located in the respective grooves 94. Respective shielding wires 44 have their outer cover 85 stripped in the vicinity of flange 78. The shield wire portion which is located behind flange 78 is tied by yarn 86 to fixing member 73 for temporary fixing. As shown in FIG. 7, the stripped portions of the shielding wires are bundled by conductor 96 as indicated by a broken line in this Figure and preparatively bonded there by means of solder 88.

The end portion of cable 98 for noise cancellation is situated within a center bore of cable fixing member 73. The outer arrangement is similar to that of the preceding embodiment.

In this embodiment, when shielding wires 44 are to be attached to cable fixing member 73 it is only necessary that shielding wires 44 be located in the respective individual grooves of fixing member 73. It is therefore possible to perform ready soldering and assembling operations and to attain a better operability and high reliability.

In the aforementioned respective embodiments, external conductors 84 of shielding wires 44 are soldered to cable fixing means 72 and 73, whereby they are electrically connected to fixing means 72 and 73 and to shield pipe 68 connected to fixing means 72 and 73. As a result, all the internal electric components are electrically shielded and thus an endoscope obtained is substantially free from an external noise. This type of endoscope can be employed so as to observe, during the use of a high frequency treatment device, a region of interest of a human being.

Figure 8:
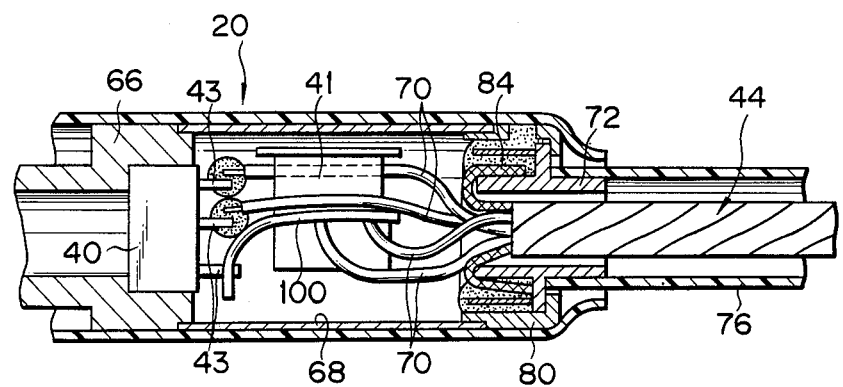
FIG. 8 is a cross-sectional view in side elevation showing a variant of a substrate for an electrical circuit section of the image sensor unit of FIG. 5.
Figure 9:
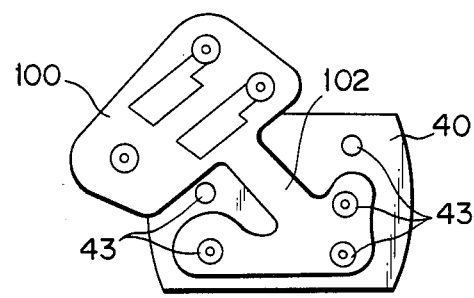
FIG. 9 is a rear view showing the substrate attached to a solid-state image sensor.

FIGS. 8 and 9 show a variant of the connection section of the solid-state image sensor. In this variant, flexible substrate 100 is soldered directly to lead-in terminals 43 of solid-state image sensor 42 and bendable narrower section 102 is provided at a portion of flexible substrate 100 and, with the flexible substrate 100 in the bent state, internal conductors 70 are soldered to flexible substrate 100, making it possible to provide a compact electric circuit section under improved operability.

Figure 10:
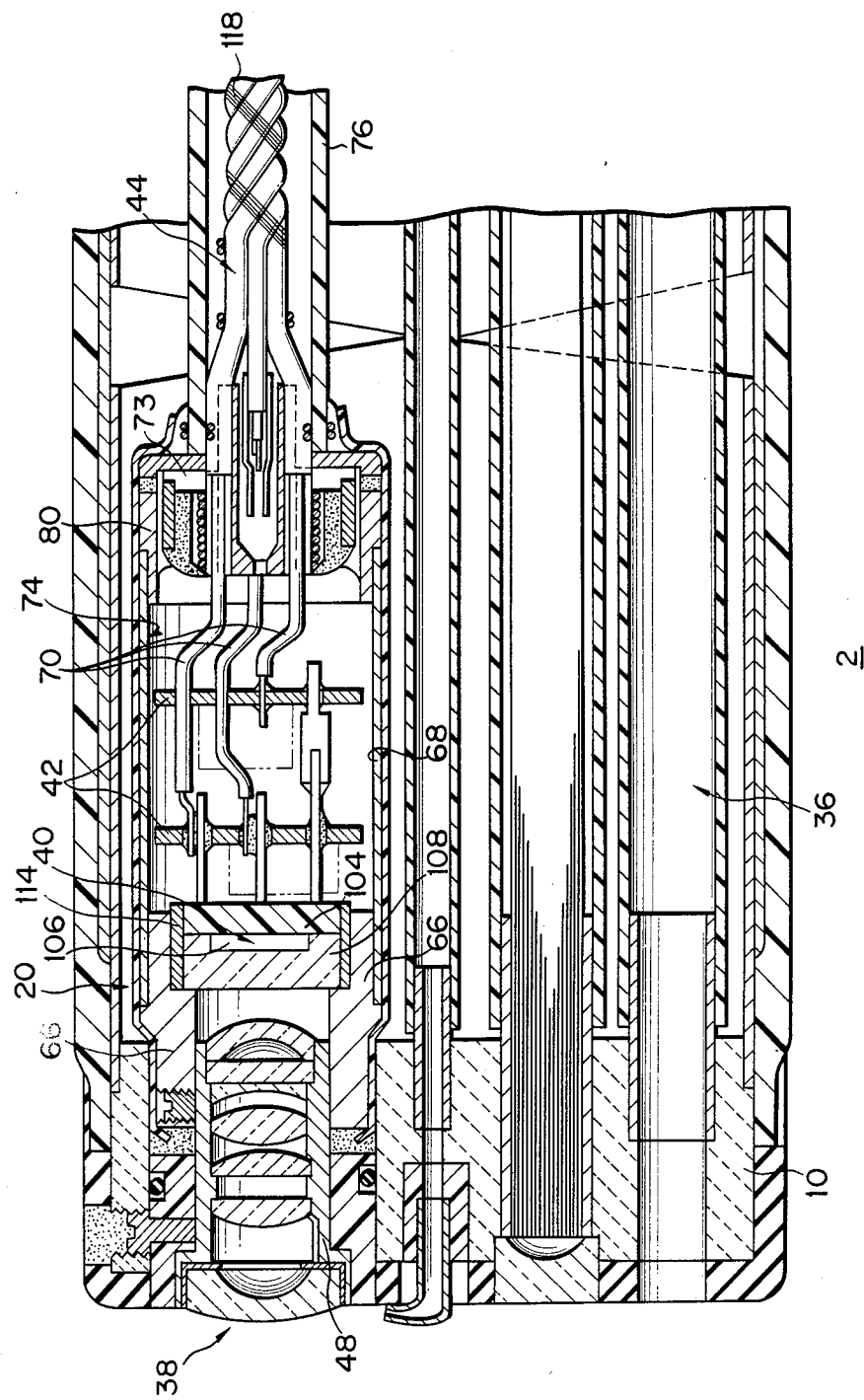
FIG. 10 is a cross-sectional view in side elevation showing a variant of the solid-state image sensor attaching section of the image sensor unit of this invention.

FIGS. 10 and 13 show a variant of the solid-state image sensor attaching section of the image sensor unit. This solid-state image sensor 40 has circular package 104 as shown in FIG. 11 and chip 106 is attached to the front center of package 104 such that it is covered with cover glass 108. A plurality of lands 110 electrically connected to chip 106 are exposed at the outer periphery of package 104 such that the lands are electrically connected to corresponding lead-in pins 43.

In this solid-state image sensor 40, insulating ring 114 as shown in FIG. 12 covers the whole outer peripheral surfaces of package 104 and cover glass 108. The insulating ring is formed of, for example, electrically insulating silicon tube or tape and completely covers the outer periphery of solid-state image sensor 40 to allow the insulating ring to be bonded to image sensor 40.

With insulating ring 114 so bonded, solid-state image sensor 40 is fitted into a recess which is provided at the rear end portion of housing 66. In this way, the image sensor is bonded to the housing.

Solid-state image sensor 40, substrates 42 and electric component parts incorporated into the substrate constitute an electric circuit section which is covered with, and electrically shielded by, shield member 74 comprised of lens frame 48, housing 66, shield pipe 68 and cable fixing member 73. A high-frequency type treating device, such as an electric knife (surgical knife), can be inserted through channel 36 of endoscope 2 into a region of interest of a human being for medical treatment, without the aforementioned electric circuit section being adversely affected by a high-frequency noise.

Furthermore, respective lands 110 of solid-state image sensor 40 are covered by insulating ring 114 and thus there is no risk of short-circuiting occurring due to the electric contacting of lands 110 with shield member 74. It is therefore possible to prevent the solid-state image sensor from being damaged.

As shown in FIG. 13, shielding wires 44 are twisted around core insulation yarn 116, such as a cotton yarn, to provide a strand around the outer periphery of which first yarn 118 is uniformly wound. First yarn 118 is wound in a direction opposite to that in which shielding wires 44 are wound. The strand and first yarn 118 are tied by second yarn 120. Adhesive 122 is coated on an overlap portion between first and second yarns 118 and 120 as shown in FIG. 13.

Solid-state image sensor 40, shield member 74 and associated electrical circuit section, together constitute one image sensor unit 20 which is detachably mounted on forward end member 10. Therefore, an assembling or servicing operation can be performed quite readily.

Figure 14:
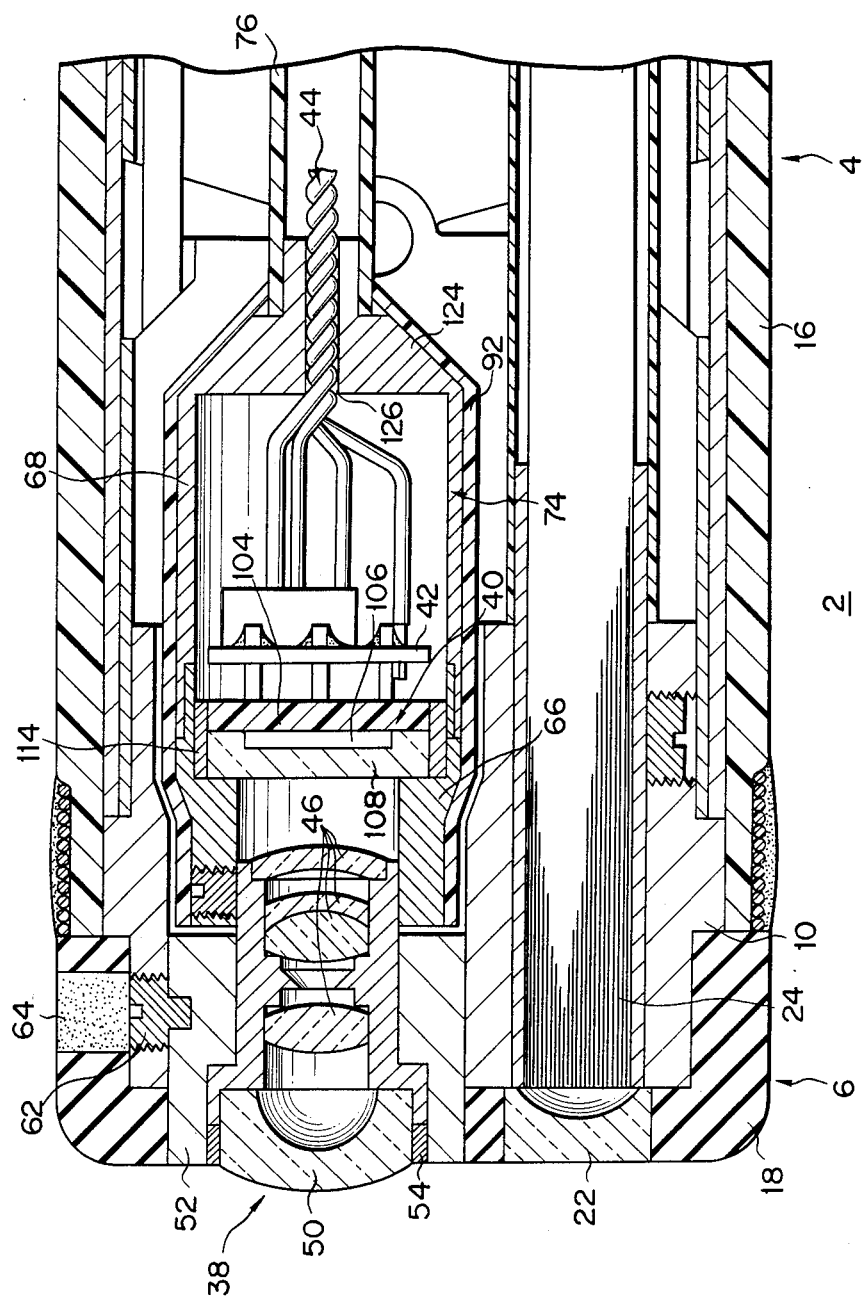
FIG. 14 is a cross-sectional view in side elevation showing a distal end portion of an endoscope according to a third embodiment of this invention.

FIG. 14 shows an endoscope according to a third embodiment of this invention. This embodiment is basically the same as the aforementioned embodiments of this invention. In this embodiment in particular, blocking wall 124 is formed integral with the rear end of shield pipe 68 and shielding wires 44 are inserted, as a cable, through a through bore (126) which is formed in blocking wall 124.

In the aforementioned endoscope of this invention, the electrical circuit section, including a solid-state image sensor incorporated into the forward end portion of the endoscope, is surrounded by the aforementioned shield member. For this reason, a high frequency type treating device, for example, can be used under a well-observable condition without being affected by noises.

What is claimed is:

1. An endoscope comprising:
    (1) an optical lens unit including a lens frame having a rear end portion, and lens frame cover and a plurality of lenses attached to the lens frame; and
    (2) an image sensor unit attached to an outer periphery of the rear end portion of the lens frame and comprising,
        (a) an electroconductive image sensor housing, one forward end portion of which is attached to the outer periphery of the rear end portion of the lens frame, the image sensor housing having a rear end portion and a recess formed there;
        (b) an electric circuit section comprised of a solid-state image sensor located within the recess and having a plurality of lead-in pins, and electric component parts electrically connected to the lead-in pins;

(c) an electroconductive shield pipe attached at a forward end portion to the outer periphery of the rear end portion of the image sensor housing and having the rearwardly extending rear end portion, the shield pipe containing the whole electric circuit section therein;

(d) electroconductive cable fixing means located behind the electric circuit section and having through recess means, the cable fixing means being fixed to the rear end portion of the shield pipe with a pipe holder therebetween; and (e) shielding wires inserted into the shield pipe through the recess means and each having an outer cover, external conductors and internal conductors electrically connected to the electric component parts or the lead-in pins.

2. An endoscope according to claim 1, in which a flexible substrate having a bendable narrow portion is soldered directly to the lead-in pins of said solid-state image sensor and said internal conductors of said shielding wires are electrically connected to said flexible substrate.

3. An endoscope according to claim 1, in which said shield pipe, said pipe holder and said cable fixing means are formed of an integral shield member.

4. An endoscope according to claim 1, in which an electrically insulating, heat-shrinkable tube is covered on the whole outer periphery of said image sensor unit.

5. An endoscope according to claim 1, in which an electrically insulating member is attached to an outer periphery of said solid-state image sensor to provide a unit, this unit being fitted into the recess of said image sensor housing.

6. An endoscope according to claim 5, in which said electrically insulating member is of a ring type.

7. An endoscope according to claim 1, in which the outer covers of said shielding wires are stripped near a middle portion of said cable fixing means to expose said external conductors, said exposed external conductors being electrically connected to said cable fixing means.

8. An endoscope according to claim 7, in which said external conductors are soldered to said cable fixing means.

9. An endoscope according to claim 7, in which said cable fixing means is formed of a metal pipe having a through hole through which said external conductors extend outwardly with their ends bonded, said cable fixing means having a flange formed on the outer periphery such that it is located at a middle portion of said cable fixing means.

10. An endoscope according to claim 9, in which said metal pipe has a circumferentially extending cutout formed at the outer periphery of a forward end portion and said external and internal conductors are tied to said metal pipe at a location of said cutout.

11. An endoscope according to claim 10, in which a solder is filled into an interstice defined among said external conductors, said metal pipe and said pipe holder.

12. An endoscope according to claim 7, in which said cable fixing means has a flange formed at an outer periphery such that it is located at a middle portion and grooves, semi-circular in cross-section, formed on the outer periphery such that they extend along an axial direction of said cable fixing means.

13. An endoscope according to claim 12, in which said shielding wires are located in corresponding cable fixing means and a conductor wire is wound on the outer periphery of said external conductors.

14. An endoscope according to claim 13, in which a solder is filled into an interstice defined among said external conductors, said cable fixing means and said pipe holder.

* * * * *